US009844451B2

United States Patent
Hershberger et al.

(10) Patent No.: US 9,844,451 B2
(45) Date of Patent: Dec. 19, 2017

(54) MODULAR TRANSDERMAL COMPRESS DEVICE

(71) Applicant: Biomet Manufacturing, LLC, Warsaw, IN (US)

(72) Inventors: Troy W. Hershberger, Winona Lake, IN (US); Joshua R. Porter, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 163 days.

(21) Appl. No.: 14/262,067

(22) Filed: Apr. 25, 2014

(65) Prior Publication Data

US 2015/0305897 A1    Oct. 29, 2015

(51) Int. Cl.
| | |
|---|---|
| *A61F 2/78* | (2006.01) |
| *A61F 2/28* | (2006.01) |
| *A61F 2/30* | (2006.01) |

(52) U.S. Cl.
CPC ............. *A61F 2/78* (2013.01); *A61F 2/2814* (2013.01); *A61F 2002/30565* (2013.01); *A61F 2002/30616* (2013.01); *A61F 2002/7887* (2013.01)

(58) Field of Classification Search
CPC ................. A61F 2/78; A61F 2002/7887; A61F 2220/0008
See application file for complete search history.

(56) References Cited

U.S. PATENT DOCUMENTS

| | | | |
|---|---|---|---|
| 3,947,897 A | 4/1976 | Owens | |
| 4,158,895 A | 6/1979 | Frosch et al. | |
| 6,197,065 B1 | 3/2001 | Martin et al. | |
| 6,508,841 B2 | 1/2003 | Martin et al. | |
| 6,712,855 B2 | 3/2004 | Martin et al. | |
| 6,869,450 B2 | 3/2005 | Grundei | |
| 7,014,661 B2 | 3/2006 | Blunn et al. | |
| 7,141,073 B2 | 11/2006 | May et al. | |
| 7,476,254 B2 | 1/2009 | White et al. | |
| 7,722,678 B2 | 5/2010 | Brown et al. | |
| 8,512,416 B2 | 8/2013 | Porter et al. | |
| 9,023,115 B2 | 5/2015 | Porter et al. | |
| 2003/0109878 A1 | 6/2003 | Grundei | |
| 2009/0149966 A1 | 6/2009 | Blunn et al. | |
| 2011/0190907 A1 | 8/2011 | Porter et al. | |

OTHER PUBLICATIONS

"Amputee Implant Devices—Osseointegration," informational website, retrieved from <http://www.amputeeimplantdevices.com> on Jun. 4, 2014. (2 sheets).
"ITAP," Retrieved from <http://www.itap-prosthetics.com> on Jun. 4, 2014. (1 sheet).

(Continued)

*Primary Examiner* — Thomas J Sweet
*Assistant Examiner* — Melissa Hoban
(74) *Attorney, Agent, or Firm* — Schwegman Lundberg & Woessner, P.A.

(57) ABSTRACT

A modular transdermal assembly configured to couple an external prosthetic device to a bone stump. The assembly includes a modular transdermal portion and a bone fixator. The modular transdermal portion includes an interface portion configured to couple with the external prosthetic device. The bone fixator is configured to be secured to the bone stump and couple with the modular transdermal portion to retain the modular transdermal portion relative to the bone stump.

20 Claims, 3 Drawing Sheets

(56) References Cited

OTHER PUBLICATIONS

"OPRA Implant System Product Catalogue," brochure. Integrum AB. (2014). 8 pages.
"The ILP Prosthesis," retrieved from <http://www.osseointegration-germany.de/index.php/en/die-ilp-prothese2_on_June_4>, 2014. (4 sheets).
Collins, L.M., "Prosthesis Method May Brighten Future for Amputees," Deseret News, reprint University of Utah School of Medicine. (Apr. 18, 2008). Retrieved from <http://medicine.utah.edu/orthopaedics/events/news/posthesismethod.htm> on May 6, 2014. (2 sheets).

MODULAR TRANSDERMAL COMPRESS DEVICE

FIELD

The present disclosure relates to a modular transdermal assembly configured to couple an external prosthetic device to a bone stump.

BACKGROUND

This section provides background information related to the present disclosure and is not necessarily prior art.

Transdermal intraosseous devices can be used to couple external prosthetic devices to a bone stump, such as subsequent to an amputation. While current transdermal intraosseous devices are suitable for their intended use, they are subject to improvement. For example, current devices may not be well suited for accommodating multiple anatomies with varying distances between a distal end of a bone stump and a distal skin area opposite thereto. The present teachings provide numerous advantages, such as, for example, a modular transdermal assembly configured to couple an external prosthetic device to a bone stump that can accommodate a variety of different separation distances between the bone stump and a distal skin area opposite thereto.

SUMMARY

This section provides a general summary of the disclosure, and is not a comprehensive disclosure of its full scope or all of its features.

The present teachings provide for a modular transdermal assembly configured to couple an external prosthetic device to a bone stump. The assembly includes a modular transdermal portion and a bone fixator. The modular transdermal portion includes an interface portion configured to couple with the external prosthetic device. The bone fixator is configured to be secured to the bone stump and couple with the modular transdermal portion to retain the modular transdermal portion relative to the bone stump.

The present teachings further provide for a modular transdermal assembly kit for coupling an external prosthetic device to a bone stump. The kit includes a plurality of modular transdermal portions of different lengths, each including an interface portion configured to couple with the external prosthetic device. The kit further includes at least one bone fixator configured to couple with the modular transdermal portion and retain the modular transdermal portion relative to the bone stump.

The present teachings also provide for a method for coupling an external prosthetic device to bone. The method includes: implanting a bone fixator in a bone stump; selecting a modular transdermal portion from a plurality of modular transdermal portions of different lengths based on a distance between the bone stump and a distal portion of skin opposite to the bone stump; coupling the selected modular transdermal portion to the bone fixator; selecting a modular skin integration component from a plurality of modular skin integration components of different geometries; and coupling the modular skin integration component to the selected modular transdermal portion proximate to the distal portion of skin.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
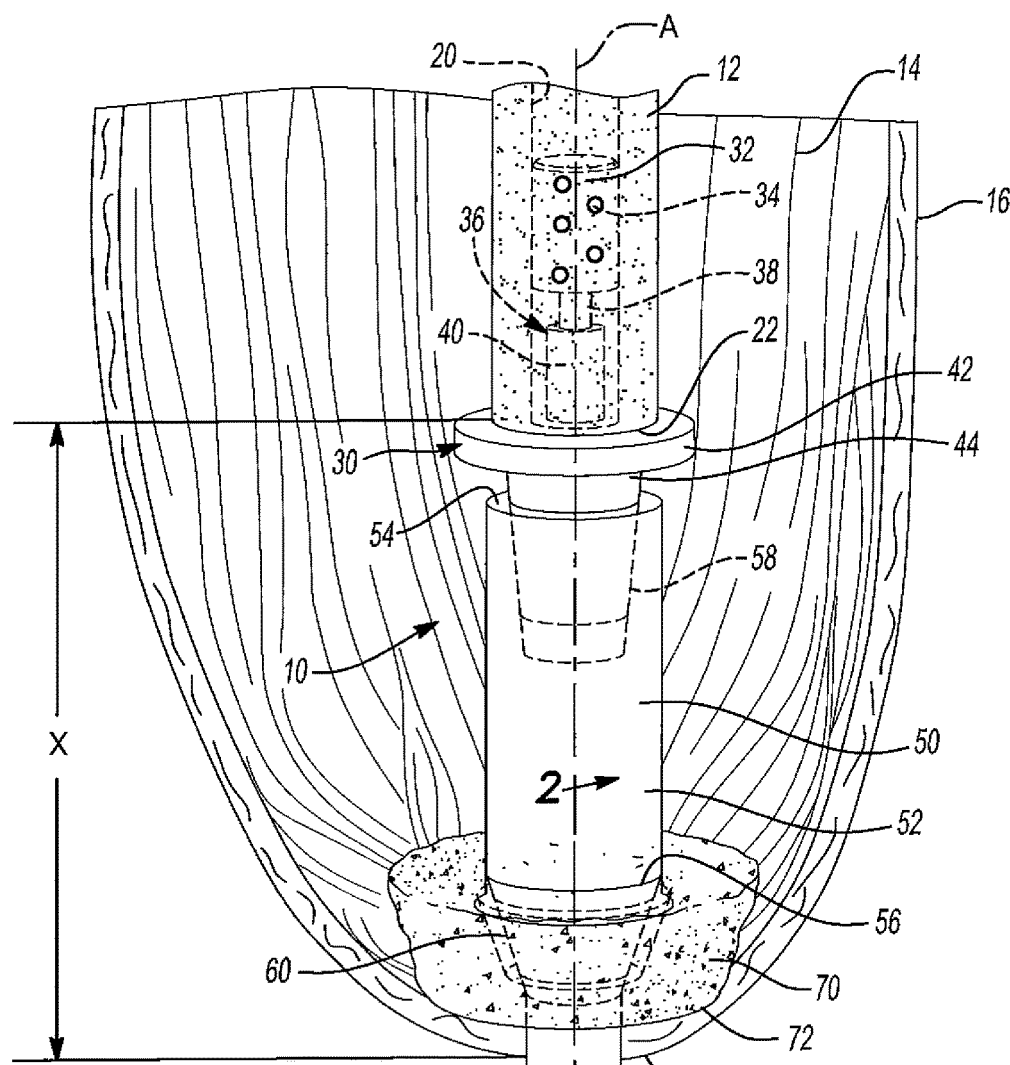
FIG. 1 is a side view of a modular transdermal assembly according to the present teachings implanted in bone.

With initial reference to FIG. 1, a modular transdermal implant assembly according to the present teachings is generally illustrated at reference numeral 10. The implant assembly 10 is illustrated as having been implanted into a bone stump 12. Extending about the bone stump 12 is muscle tissue 14 and skin 16. A distal area of the skin 16 is at, and proximate to, reference numeral 18. Between the bone stump 12 and the distal skin area 18 is a soft tissue envelope having a length X of the anatomy illustrated. The length X can vary depending on the patient's anatomy. The bone stump 12 defines an intramedullary canal 20, which extends to a distal end 22 of the bone stump 12.

The modular transdermal implant assembly 10 includes a bone fixator 30. The bone fixator 30 includes a bone anchor 32, which can be an anchor plug. The bone anchor 32 can be secured within the intramedullary canal 20 in any suitable manner and with any suitable device, such as with bone pins 34.

Extending distally from the bone anchor 32 is an elongated rod 36. The elongated rod 36 includes a small diameter portion 38 and a large diameter portion 40. The small diameter portion 38 is between the large diameter portion 40 and the bone anchor 32. Extending from the large diameter portion 40 is a bone collar 42. Extending distally from the bone collar 42 is a coupling portion or flange 44, which can include a tapered coupling flange as illustrated. The bone collar 42 can have any suitable size or shape, such as a disc-like shape as illustrated, which has a diameter larger than a diameter of the bone stump 12 at the distal end 22 thereof. The bone fixator 30 can be made of any suitable biocompatible material, such as any suitable metal.

The modular transdermal implant assembly 10 further includes a modular transdermal portion 50, which includes an elongated body or shaft portion 52. The elongated body portion 52 includes a proximal end 54 and a distal end 56 opposite thereto. Extending from the distal end 56 is a tapered portion 60. Extending distally from the tapered portion 60 is an external adapter or connector 62. Therefore, the tapered portion 60 is between the elongated body portion 52 and the external adapter 62.

The external adapter 62 includes a prosthetic interface portion 64 at a distal end thereof. The prosthetic interface portion 64 can include any suitable coupling portion or member, such as flattened surfaces 66 as illustrated. The prosthetic interface portion 64 is configured to couple any suitable prosthetic device to the modular transdermal implant assembly 10, and at the distal skin area 18 of the patient. The prosthetic device can be any suitable prosthetic device, such as a prosthetic leg, foot, arm, or hand.

The modular transdermal portion 50 can have any suitable length depending on the patient's anatomy, such as depending on the length of the soft tissue envelope as measured based on the distance between the distal end 22 of the bone stump 12 and the distal skin area 18. The modular transdermal portion 50 can be included in a kit including a plurality of modular transdermal portions 50 of different lengths. The modular transdermal portion 50 with the most appropriate length based on the patient's anatomy can be selected and implanted as illustrated in FIG. 1, for example. Any portion of the modular transdermal portion 50 can be provided with varying lengths to best fit the patient's anatomy.

Figure 4:
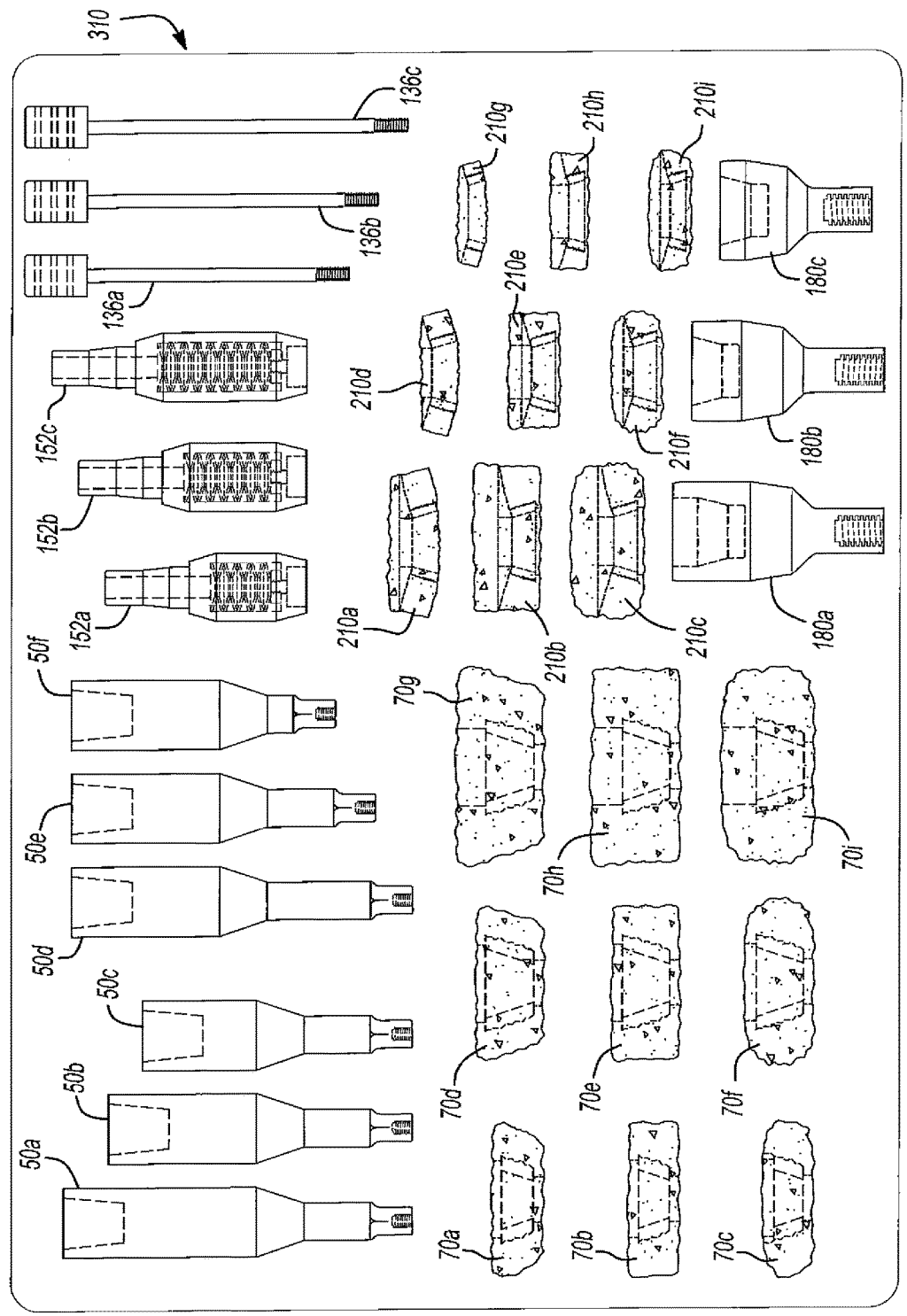
FIG. 4 is a modular transdermal assembly kit according to the present teachings.

For example, the elongated body portion 52 can have any suitable length between the proximal end 54 and the distal end 56 along the longitudinal axis A. Thus, a plurality of modular transdermal portions 50 with varying lengths of the elongated body portion 52 between the proximal and distal ends 54 and 56 along the longitudinal axis A can be provided, as illustrated at reference numbers 50a-50c in the exemplary kit 310 of FIG. 4. The tapered portion 60 and/or the external adapter 62 can each be provided with different lengths along the longitudinal axis A as well. For example, transdermal portions 50d-50f of the kit 310 have external adaptors 62 of different lengths. Thus kit 310 including a plurality of the modular transdermal portions 50a-50f can be provided in which the plurality of modular transdermal portions 50 included with the kit have varying lengths along the longitudinal axis A at any one or more of the elongated body portion 52, the tapered portion 60, and the external adapter 62.

The modular transdermal portion 50 can be coupled to the bone fixator 30 in any suitable manner. For example, the modular transdermal portion 50 can be coupled to the coupling flange 44 by arranging the modular transdermal portion 50 such that the male coupling flange 44 extends into female coupling receptacle 58 of the elongated body portion 52 and is secured therein with a taper lock, such as a Morse taper lock. The coupling configuration can also be reversed, for example, such that the coupling flange 44 extends from the proximal end 54 of the elongated body portion 52 into the coupling receptacle 58 included with the bone fixator 30.

The modular transdermal implant assembly 10 can further include an annular modular skin integration component 70. The modular skin integration component 70 includes a skin ingrowth surface 72, which can be made of any suitable material configured to permit skin growth therein in order to enhance fixation of the modular transdermal implant assembly 10 to surrounding skin 16, such as at the distal skin area 18. For example, the skin ingrowth surface 72 can be made of any suitable porous material, roughened material, etc.

Figure 2:
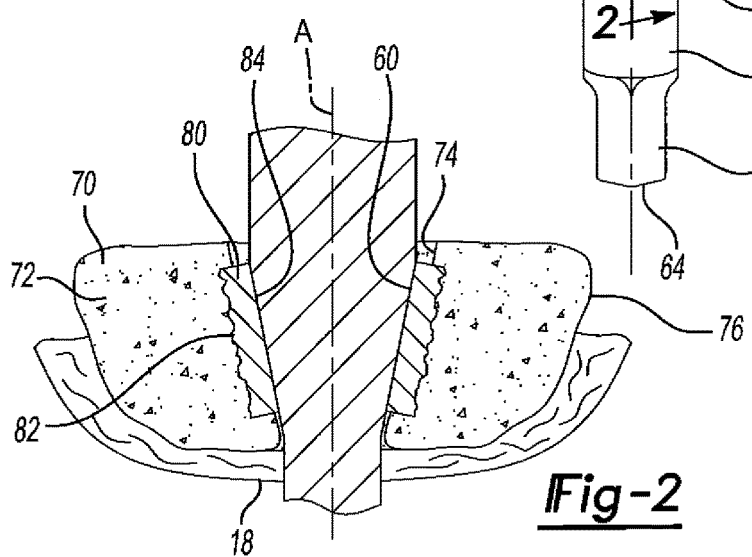
FIG. 2 is a cross-sectional view of FIG. 1 taken along line 2-2 of FIG. 1.

With additional reference to FIG. 2, the modular skin integration component 70 is generally annular and defines a center bore 74. The center bore 74 is generally tapered in the proximal to distal direction and includes a coupling member 80 seated therein. The coupling member 80 includes a roughened outer surface 82 and an inner tapered surface 84 opposite thereto. The roughened outer surface 82 engages the skin ingrowth surface 72 in order to facilitate retention of the coupling member 80 within the center bore 74. The inner tapered surface 84 can be solid, smooth, and tapered at an angle generally corresponding to the tapered portion 60 of the modular transdermal portion 50 such that upon passing the modular skin integration component 70 over the external adapter 62 and onto the tapered portion 60, the modular skin integration component 70 will be coupled to the tapered portion 60, such as with a taper lock.

The modular skin integration component 70, and particularly the skin ingrowth surface 72 thereof, can have any suitable size or shape to accommodate the patient's anatomy. The modular skin integration component 70 can be included in a kit having a plurality of modular skin integration components 70, each with a different size and/or shape. For example, the kit 310 can include a plurality of modular skin integration components 70a-70i having different shapes (such as tapered, rounded, or with straight edges 76), different lengths along the longitudinal axis A, and different widths as measured extending outward and generally perpendicular to the longitudinal axis A. The modular skin integration component 70 best suited for the patient's anatomy can be selected from the kit and coupled to the modular transdermal portion 50 at the tapered portion 60 as appropriate. This modularity provides a surgeon with multiple ingrowth geometries to match or approximate the patient's soft tissue envelope. This also allows the modular transdermal portion 50 to be manufactured without the need to be sintered and/or without additive manufacturing, both of which may have a lower fatigue strength compared to wrought Ti-6-4 or Co—Cr, which the modular transdermal portion 50 can be made of pursuant to the present teachings.

Figure 3:
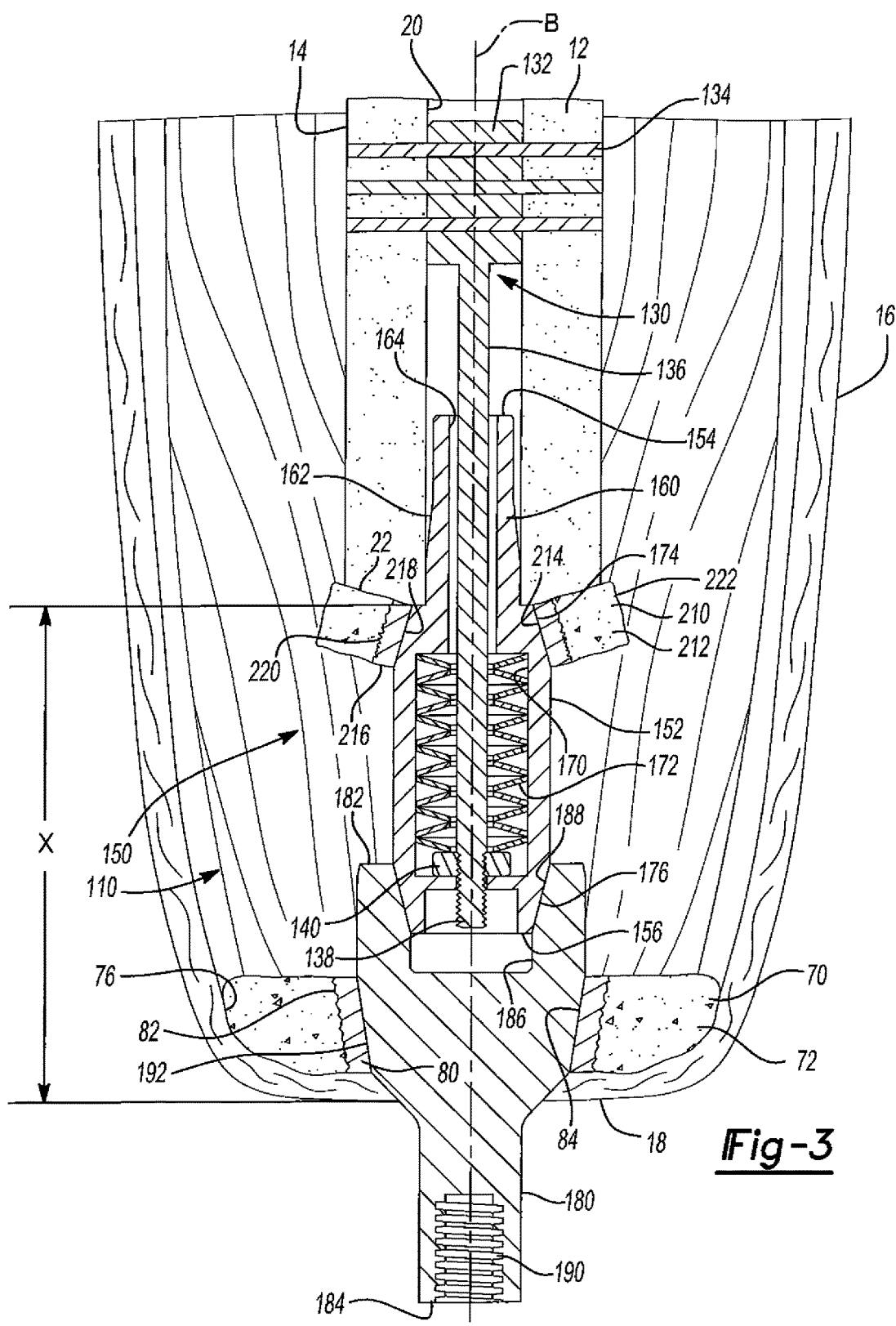
FIG. 3 is a cross-sectional view of another modular transdermal assembly according to the present teachings implanted in bone.

Another modular transdermal implant assembly according to the present teachings is illustrated in FIG. 3 at reference numeral 110. Like the modular transdermal implant assembly 10, the assembly 110 is illustrated implanted in bone stump 12 defining an intramedullary canal 20. The modular transdermal implant assembly 110 includes a bone fixator 130 including a bone anchor 132, which can be secured within intramedullary canal 20 of the bone stump 12 in any suitable manner, such as with bone pins 134. The bone anchor 132 can be any suitable device for anchoring the modular transdermal implant assembly 110 within the intramedullary canal 120 of the bone stump 12, such as an anchor plug. Extending from the bone anchor 132 is a coupling portion in the form of a variable length rod 136, the length of which can vary along longitudinal axis B. The kit 310 can include a plurality of rods 136a-136c having different lengths along the longitudinal axis B. The variable length rod 136 includes a threaded portion 138 at a distal end thereof. Connected to the coupling portion 136 at the threaded portion 138 is a suitable fastener, such as a nut 140.

The modular transdermal implant assembly 110 further includes a modular transdermal portion 150, which includes an elongated body portion or shaft 152 having a proximal end 154 and a distal end 156. At the proximal end 154 is a proximal flange 160 with an outer tapered surface 162. The proximal flange 160 defines a bore 164 extending from the proximal end 154 to a receptacle 170 defined by the elongated body portion 152. Within the receptacle 170 are a plurality of compression members 172.

The compression members 172 can be any suitable compliant member, such as a plurality of Bellville washers, with neighboring ones of the compression members 172 arranged opposite to one another. Each one of the compression members defines a center aperture through which the coupling portion 136 extends. The fastener 140 is seated against a distal end of the most distal compression member 172.

Thus with the bone anchor 132 secured within the intramedullary canal 20, the compression members 172 provide the modular transdermal implant assembly 110 with a compliant fixator, which in turn provides a bone biasing force against distal end 22 of the bone stump 12. This bone biasing force can provide a compressive load on the bone stump 12, which can result in reduced bone loss and can promote bone growth, for example. Compliance of the bone fixator 130 can exceed that of native bone, such that stress shielding does not occur. Any suitable compliant fixator can be used, including, but not limited to, the compliant fixators disclosed in commonly assigned U.S. Pat. Nos. 7,722,678; 7,141,043; 6,712,855; 6,508,841; and 6,197,065, all of which are assigned to common Assignee Biomet Manufacturing Corp. of Warsaw, Ind., and are incorporated herein by reference.

The elongated body portion 152 can be provided with any suitable length, depending on the patient's anatomy. For example, the kit 301 can include a plurality of the elongated body portions 152a-152c having different lengths along the longitudinal axis B, which can be selected to accommodate the patient's anatomy, such as the distance X between the distal end 22 of the bone stump 12 and the distal skin area 18 of the patient's soft tissue envelope. Furthermore, the compression members 172 can be stacked at any suitable height within the receptacle 170 to vary the distance between the bone anchor 132 and the elongated body portion 152 in view of the length of the bone stump 12. This may be advantageous if a secondary or revision "tightening" of the modular transdermal implant assembly 110 is appropriate, such as in view of degradation (i.e., shortening) of the bone stump 12.

The elongated body portion 152 further includes, at outer surfaces thereof, a proximal tapered surface 174 and a distal tapered surface 176. Coupled to the distal tapered surface 176 is a modular transdermal adaptor or connector 180. The transdermal adapter 180 includes a proximal end 182 and a distal end 184 opposite thereto. The transdermal adaptor 180 can be selected from a plurality of transdermal adaptors 180a-180c of kit 310 having different lengths along the longitudinal axis B to best fit the patient's soft tissue envelope, such as the distance X between the distal end 22 of the bone stump 12 and the distal skin area 18 of the patient's soft tissue envelope. At the proximal end 182, the transdermal adapter 180 defines a receptacle 186, which includes an internal tapered surface 188 extending distally from the proximal end 182. At the distal end 184 is a prosthetic interface portion 190, which can be any suitable portion or device configured to retain any suitable prosthetic to the transdermal adapter 180, such as a prosthetic leg, foot, arm, or hand. As illustrated, the prosthetic interface portion 190 is threaded to receive threads of the prosthetic device.

The elongated body portion 152 is received within the transdermal adapter 180 such that the distal tapered surface 176 of the elongated body portion 152 mates with the internal tapered surface 188 of the transdermal adapter 180 to secure the elongated body portion 152 and the transdermal adapter 180 together, such as with a taper lock. The elongated body portion 152 and the transdermal adapter 180 can be coupled together in any other suitable manner as well.

The transdermal adapter 180 further includes an intermediate outer tapered surface 192 between the proximal end 182 and the distal end 184. The intermediate outer tapered surface 192 is sized and shaped to cooperate with the inner tapered surface 84 of the modular skin integration component 70 in order to couple the modular skin integration component 70 to the transdermal adapter 180 in any suitable manner, such as with a taper lock. When the modular skin integration component 70 is included in the kit 302 of a plurality of modular skin integration components 70 of different sizes and shapes, such as components 70a-70i, any one of the modular skin integration components 70 of the kit may be coupled to the transdermal adapter 180 to accommodate the patient's anatomy.

The modular transdermal implant assembly 110 further includes a modular bone integration component 210 including bone ingrowth material 212. The bone ingrowth material 212 can be any suitable material configured to permit growth of bone therein to enhance fixation of the modular bone integration component 210 to the bone stump 12. For example, the bone ingrowth material 212 can be made of materials that are porous, roughened, etc. The modular bone integration component 210 defines an inner tapered surface 214 to which a coupling member 216 is mounted. The coupling member 216 can be made of any suitable material, such as a metallic material, and includes a tapered surface 218 configured to mate with the proximal tapered surface 174 of the elongated body portion 152 in order to couple the modular bone integration component 210 to the elongated body portion 152. The tapered surface 218 can be smooth and solid. A roughened surface 220 can be included opposite to the tapered surface 218 to secure the coupling member 216 to the modular bone integration component 210.

The modular bone integration component 210 can have any suitable size or shape to accommodate the patient's anatomy, such as the anatomy at the distal end 22 of the bone stump 12. The kit 310 may include a plurality of modular bone integration components 210a-i, each having different sizes and/or shapes, which can be selected for implantation based on the patient's anatomy. The modular bone integration components 210a-210i can have different shapes (such as tapered, rounded, or with straight edges 222), different lengths along the longitudinal axis A, and different widths as measured extending outward and generally perpendicular to the longitudinal axis A.

The present teachings further provide for a method for coupling the external prosthetic device to the bone stump 12. The method can include implanting the bone fixator 30 or 130 in the bone stump 12. The modular transdermal portion 50 or 150 is selected from a plurality of modular transdermal portions of different lengths, such as 50a-50f or elongated body portions 152a-152c, based on a distance between the bone stump 12 and the distal portion of skin opposite 18 to the bone stump 12. The selected modular transdermal portion 50a-50f or body portion 152a-152c is coupled to the bone fixator 30 or 130. The modular skin integration component 70 is selected from a plurality of modular skin integration components 70a-70i of different geometries. The modular skin integration component 70a-70i is then coupled to the selected modular transdermal portion 50 or 150 proximate to the distal portion 18 of skin 16, such as with a taper lock. A modular bone integration component 210a-210i can be selected from a plurality of different bone integration components 210a-210i of different shapes and sizes as described above, and can be coupled to the selected modular transdermal portion 50 or 150 proximate to the bone stump 12, such as with a taper lock.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular transdermal assembly configured to couple an external prosthetic device to a bone stump comprising:
   a modular transdermal portion including an interface portion configured to couple with the external prosthetic device, the modular transdermal portion having an outer tapered surface; and
   a bone fixator configured to be secured to the bone stump and couple with the modular transdermal portion to retain the modular transdermal portion relative to the bone stump; and
   a modular skin integration component configured to couple with the modular transdermal portion, the modular skin integration component having an annular shape defining a center bore, wherein the center bore includes an inner tapered surface sized and shaped to interface with the outer tapered surface of the modular transdermal portion;
   wherein the modular transdermal portion is selected from a plurality of modular transdermal portions having different lengths to have a desired length based on a distance between a distal end of the bone stump and a distal portion of skin opposite to the distal end of the bone stump.

2. The modular transdermal assembly of claim 1, wherein the modular transdermal portion includes a transdermal shaft including a first coupling portion configured to couple with the bone fixator and a second coupling portion configured to couple with the external prosthetic device, the first and second coupling portions are at opposite ends of the transdermal shaft.

3. The modular transdermal assembly of claim 2, wherein the transdermal shaft is selected from a plurality of transdermal shafts having different lengths based on a distance between a distal end of the bone stump and a distal portion of skin opposite to the distal end of the bone stump.

4. The modular transdermal assembly of claim 2, wherein the first coupling portion is a tapered receptacle configured to receive a tapered coupling flange of the bone fixator to couple the transdermal shaft to the fixator with a taper lock.

5. The modular transdermal assembly of claim 1, wherein the modular transdermal portion includes a shaft configured to be coupled to the bone stump with the bone fixator, and a transdermal adaptor including the interface portion.

6. The modular transdermal assembly of claim 5, wherein the shaft includes a tapered surface at a distal end thereof, and the transdermal adaptor defines an internally tapered surface configured to mate with the tapered surface of the shaft to secure the transdermal adaptor to the shaft with a taper lock.

7. The modular transdermal assembly of claim 5, wherein the bone fixator includes an anchor plug and an elongated rod extending therefrom, the rod configured to couple with the shaft to couple the shaft to the bone.

8. The modular transdermal assembly of claim 5, wherein the shaft defines a receptacle housing a plurality of tension-absorbing washers.

9. The modular transdermal assembly of claim 1, wherein the modular transdermal portion has a proximal end and a distal end, the interface portion of the modular transdermal portion being proximate the distal end of the modular transdermal portion, the outer tapered surface of the modular transdermal portion facing toward the distal end, and the inner tapered surface of the modular skin integration component facing toward the proximal end of the modular transdermal portion, wherein the modular skin integration component restrains distal movement of the modular transdermal portion.

10. The modular transdermal assembly of claim 1, wherein the modular skin integration component is selected from a plurality of modular skin integration components of different lengths relative to a longitudinal axis of the modular transdermal assembly, each of which have a skin in-growth surface with a different geometry that can be selected based on a patient's soft tissue envelope.

11. The modular transdermal assembly of claim 1, further comprising a coupling member seated between the modular transdermal portion and the modular skin integration component.

12. The modular transdermal assembly of claim 11, wherein the coupling member includes a roughened outer surface configured to engage the modular skin integration component, and includes an inner tapered surface sized and shaped to interface with the outer tapered surface of the modular transdermal portion.

13. The modular transdermal assembly of claim 1, further comprising a modular bone collar configured to couple with the modular transdermal portion and abut the bone stump, the modular bone collar selected from a plurality of different bone collars with bone in-growth portions having different geometries.

14. A modular transdermal assembly system for coupling an external prosthetic device to a bone stump comprising:
   a plurality of modular transdermal portions of different lengths, each including an interface portion configured to couple with the external prosthetic device and an outer tapered surface, wherein one or more of the modular transdermal portions of a desired length can be selected based on a distance between a distal end of the bone stump and a distal portion of skin opposite to the distal end of the bone stump;
   at least one bone fixator configured to couple with the one or more modular transdermal portions and retain the one or more modular transdermal portions relative to the bone stump; and
   one or more modular skin integration components configured to couple with the one or more modular transdermal portions, the one or more modular skin integration components each having an annular shape defining a center bore, wherein the center bore includes an inner tapered surface sized and shaped to interface with the outer tapered surface of the one or more modular transdermal portions.

15. The modular transdermal assembly system of claim 14, wherein each one of the plurality of modular transdermal portions includes a transdermal shaft having a first coupling portion configured to couple with the at least one bone fixator and a second coupling portion configured to couple with the external prosthetic device, the first and second coupling portions are at opposite ends of the transdermal shaft.

16. The modular transdermal assembly system of claim 14, the one or more modular skin integration components each having different geometries and each configured to individually couple with the plurality of modular transdermal portions.

17. A modular transdermal assembly:
   a bone fixator configured to be secured to a bone stump;
   a modular transdermal portion including an implant portion configured to be coupled to the bone fixator, and an interface portion configured to couple with an external prosthetic device, the implant portion including an outer tapered surface; and a modular skin integration component including an annular shape defining a center bore, wherein the center bore includes an inner tapered surface configured to couple with the outer tapered surface of the implant portion of the modular transdermal portion;

wherein the modular transdermal portion is selected from a plurality of modular transdermal portions having different lengths to have a desired length based on a distance between a distal end of the bone stump and a distal portion of skin opposite to the distal end of the bone stump.

18. The modular transdermal assembly of 17, wherein the modular transdermal portion includes:

an elongated body portion including a proximal end and a distal end, the proximal end configured to be coupled to the bone fixator, and a modular transdermal adaptor including a proximal end and distal end, the proximal end of the modular transdermal adaptor configured to couple with the distal end of the elongated body portion, and the distal end of the modular transdermal adaptor configured to couple with the external prosthetic device.

19. The modular transdermal assembly of claim 18, wherein the elongated body portion includes a distal tapered surface, and the modular transdermal adaptor includes an internal tapered surface, the internal tapered surface of the modular transdermal adaptor configured to mate with the distal tapered surface of the elongated body portion.

20. The modular transdermal assembly of claim 17, wherein the modular transdermal portion includes portions defining a bore and a receptacle, and the bone fixator includes a rod sized and shaped to extend through the bore and the receptacle, the modular transdermal assembly further comprising a plurality of compression members in the receptacle, and a compression element coupled to a distal portion of the rod, the compression element engaged with the compression members.

* * * * *

UNITED STATES PATENT AND TRADEMARK OFFICE
CERTIFICATE OF CORRECTION

PATENT NO. : 9,844,451 B2
APPLICATION NO. : 14/262067
DATED : December 19, 2017
INVENTOR(S) : Hershberger et al.

Page 1 of 1

It is certified that error appears in the above-identified patent and that said Letters Patent is hereby corrected as shown below:

In the Claims

In Column 9, Line 15, in Claim 18, after "of", insert --claim--

Signed and Sealed this
Second Day of April, 2019

Andrei Iancu
*Director of the United States Patent and Trademark Office*